United States Patent
Szpekman

(10) Patent No.: US 7,188,485 B2
(45) Date of Patent: Mar. 13, 2007

(54) DEVICE FOR CONDITIONING AIR BY MEANS OF SPRAYING AT LEAST ONE LIQUID PRODUCT

(75) Inventor: Cesar Miguel Szpekman, Tucumán (AR)

(73) Assignee: Smellgood LLC, Surfside, FL (US)

( * ) Notice: Subject to any disclaimer, the term of this patent is extended or adjusted under 35 U.S.C. 154(b) by 197 days.

(21) Appl. No.: 10/946,168

(22) Filed: Sep. 21, 2004

(65) Prior Publication Data

US 2006/0060990 A1 Mar. 23, 2006

(51) Int. Cl.
*F28D 5/00* (2006.01)
(52) U.S. Cl. .......................................... 62/304; 454/157
(58) Field of Classification Search .................. 62/121, 62/126, 171, 176.4, 304, 314, 402; 261/34.1, 261/97, 98, 110, 111; 239/332; 222/333, 222/383.1, 504; 454/74, 157, 328
See application file for complete search history.

(56) References Cited

U.S. PATENT DOCUMENTS

| | | | | |
|---|---|---|---|---|
| 4,135,647 A | * | 1/1979 | Mascia et al. | 222/211 |
| 4,162,037 A | * | 7/1979 | Koyama | 239/332 |
| 4,617,157 A | * | 10/1986 | Stein et al. | 261/96 |
| 5,150,841 A | * | 9/1992 | Silvenis et al. | 239/332 |
| 5,346,132 A | * | 9/1994 | Hahn et al. | 239/71 |
| 5,377,363 A | * | 1/1995 | Shieh | 4/313 |
| 5,466,399 A | * | 11/1995 | Von Kempski et al. | 261/27 |
| 5,505,378 A | * | 4/1996 | Park | 236/49.3 |
| 5,676,283 A | * | 10/1997 | Wang | 222/649 |
| 5,704,832 A | * | 1/1998 | Borrell | 454/157 |
| 5,893,515 A | * | 4/1999 | Hahn et al. | 239/17 |
| 6,766,650 B2 | * | 7/2004 | Cunha et al. | 62/68 |
| 6,769,580 B2 | * | 8/2004 | Muderlak et al. | 222/646 |

FOREIGN PATENT DOCUMENTS

JP 5-126690 A * 5/1993
WO WO 82/03378 * 10/1982

* cited by examiner

*Primary Examiner*—Mohammad M. Ali
(74) *Attorney, Agent, or Firm*—Greer, Burns & Crain, Ltd.

(57) ABSTRACT

A device is provided for conditioning air by controllably delivering liquid products in a room, a mall, a hospital, a factory, a cinema, an office, a theatre or any similar building, facility. The device includes at least a motor driven electromechanical liquid sprayer and a motor connected to at least a device-operation programming circuit. This programming circuit includes several timers for driving the motor according to programmed data as to start time, end time, sequential activation frequency, length of each sequential activation, etc. The device may be used both for aromatizing and disinfecting and for any procedure requiring spraying liquid products in any room or facility.

20 Claims, 4 Drawing Sheets

DEVICE FOR CONDITIONING AIR BY MEANS OF SPRAYING AT LEAST ONE LIQUID PRODUCT

BACKGROUND OF THE INVENTION

1. Field of the Invention

The present invention relates to a device for controllably delivering liquid products in rooms by means of atomization, vaporization, pulverization, spraying or the like, and more particularly relates to a device preferably able to aromatize, among another implementations, both large rooms that have previously installed forced ventilation systems, as fan blowers, air extractors, air conditioning systems or any other device intended for circulating air, and rooms where it is intended to simultaneously install said circulating air systems and the device of the present invention.

2. Description of the Prior Art

Referring to the prior art, it is possible to mention that most of the room aromatizing devices that are known nowadays are hand-operated, for instance room deodorants or perfumes in atomizing containers. Thus, it is the user who personally has to manually operate said aromatizing devices; by pressing or actuating valves or other mechanisms in order to disperse the odoriferous content in the room.

Other devices intended for atomizing liquid products in large rooms, characterized by the new features of the device of the present invention, were not known until now. These features will be disclosed in this document.

Indeed, among the most outstanding advantages of the present invention it is possible to cite that, manufacturing it is easy and inexpensive, its trouble-free use, and the present device is highly effective for aromatizing large rooms in a manner that was impossible to achieve until now.

Even though, as it has been mentioned above, the device of the present invention has been especially directed to atomizing aromatic liquids in large rooms, as supermarkets, shopping centers, galleries, etc., this device can be used in any place where a forced ventilation system is installed, for instance shops, offices, homes, ships, planes, buses, trains, subways, etc. Additionally, this device can be used with diverse featured liquid products, without regard of its fragrance, intensity of aroma, kind of fragrance, trademark, etc., according to what the user desires and the desired environmental conditions.

Even when the preferred use of the device is for aromatizing, this device can also be for atomizing other liquid products, as such insecticides, bactericides, fungicides, etc., obviously its application being adjusted according to the particular application.

SUMMARY OF THE INVENTION

It is therefore an object of the invention to provide a device for atomizing liquid products in rooms, particularly for aromatizing large rooms, wherein using the device combining mechanical and electronic parts, it is possible to spray an aromatic substance in the room, which will be spread onto the whole room by means of the forced ventilation systems, no matter the size of the room nor the number of devices, since said forced ventilation systems' extractors will take the aromatized air and spread it everywhere in the room.

It is still another object of the present invention to provide a room-aromatizing device able to dose the amount of aromatic substance spread in the room, controlling by means of electronics the aromatizing schedule and time, as well as the quantity and type of aromatic products used in the process.

It is a further object of the present invention to provide a device for controllably delivering liquid products in rooms by means of atomization, vaporization, pulverization or the similar, of the type that includes an electric-motor driven sprayer, having a pulverizable liquid input and a pulverized liquid output, having a liquid substances container connected to said sprayer, wherein the sprayer comprises at least an electromechanical liquids sprayer and said motor is connected to at least a device-operation programming circuit, which comprises a programmable electronic controller including a first timing circuit (timer) which defines the start time and the operation time of the electromechanical sprayer's driving motor, a second timer that defines the sequential activation frequency of said motor, and a third timer that defines the length of each sequential activation cycle of said motor by means of the second timer.

BRIEF DESCRIPTION OF THE DRAWINGS

The present invention is illustrated by way of example in the following drawings wherein.

DESCRIPTION OF THE PREFERRED EMBODIMENTS

In the description below the term "spraying" will be generically used and has to be understood as referring to any way and/or method for obtaining in-suspension particles in the air.

The device of the invention can be installed in several kinds of forced ventilation systems. In case of being installed in central air conditioners, the device is placed inside the air conditioner, with the sprayed liquid mist aimed in the direction of the air conditioner filter. Thus, as a result of the direction of the airflow, the sprayed liquid is impelled towards the air conditioner outlets. In an equal manner, the device of the invention might be installed anywhere in the air flow generated by any forced ventilation system, no matter if it is inside or outside said system. Moreover, the device is operable while located on the floor.

Figure 1:
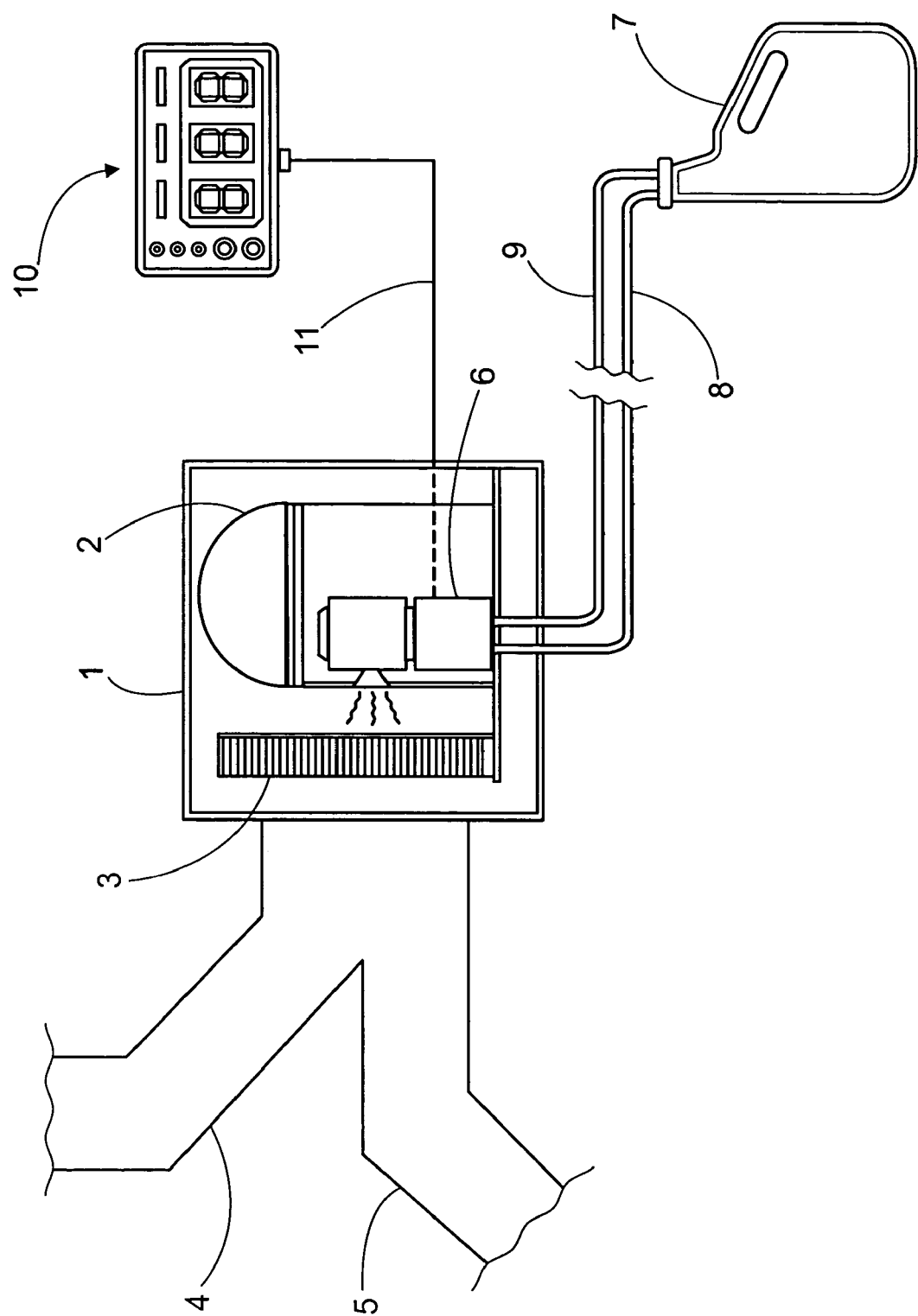
FIG. 1 is a basic diagram corresponding to the device of the invention installed in a central air conditioning system.

FIG. 1 shows a central air conditioning device that includes a compressor 2, an air outlet filter grid 3 and two air distribution conduits 4 and 5 wherein the liquid products will be sprayed. A liquids sprayer 6 is shown behind the grid 3. This sprayer 6 is driven by an electric motor, which generally comprises an electromagnet operating a plate that drives a piston that aspirates liquid products from a container and compresses them in order to spray said liquid products. The liquid or fluid is held into a container or jerrycan 7 that is connected with the sprayer 6 by means of conduits. These conduits include a first conduit 8 whereby liquid flows from the container 7 to the sprayer 6, and a second conduit 9 whereby excess liquid flows back from the sprayer 6 to the container 7.

A programming panel commands the sprayer 6 and particularly its electric motor. This panel 6 is connected with said motor by means of cables 11, and includes the required components to make it programmable, as will be explained later.

The air-forcing fan has not been illustrated in FIG. 1 for better understanding.

In order to contain the liquid that will be sprayed, any kind of suitable container may be used without regard to size or material. For instance, suitable containers include a plastic or metallic jerrycan 7, a bottle, etc.

Figure 2:
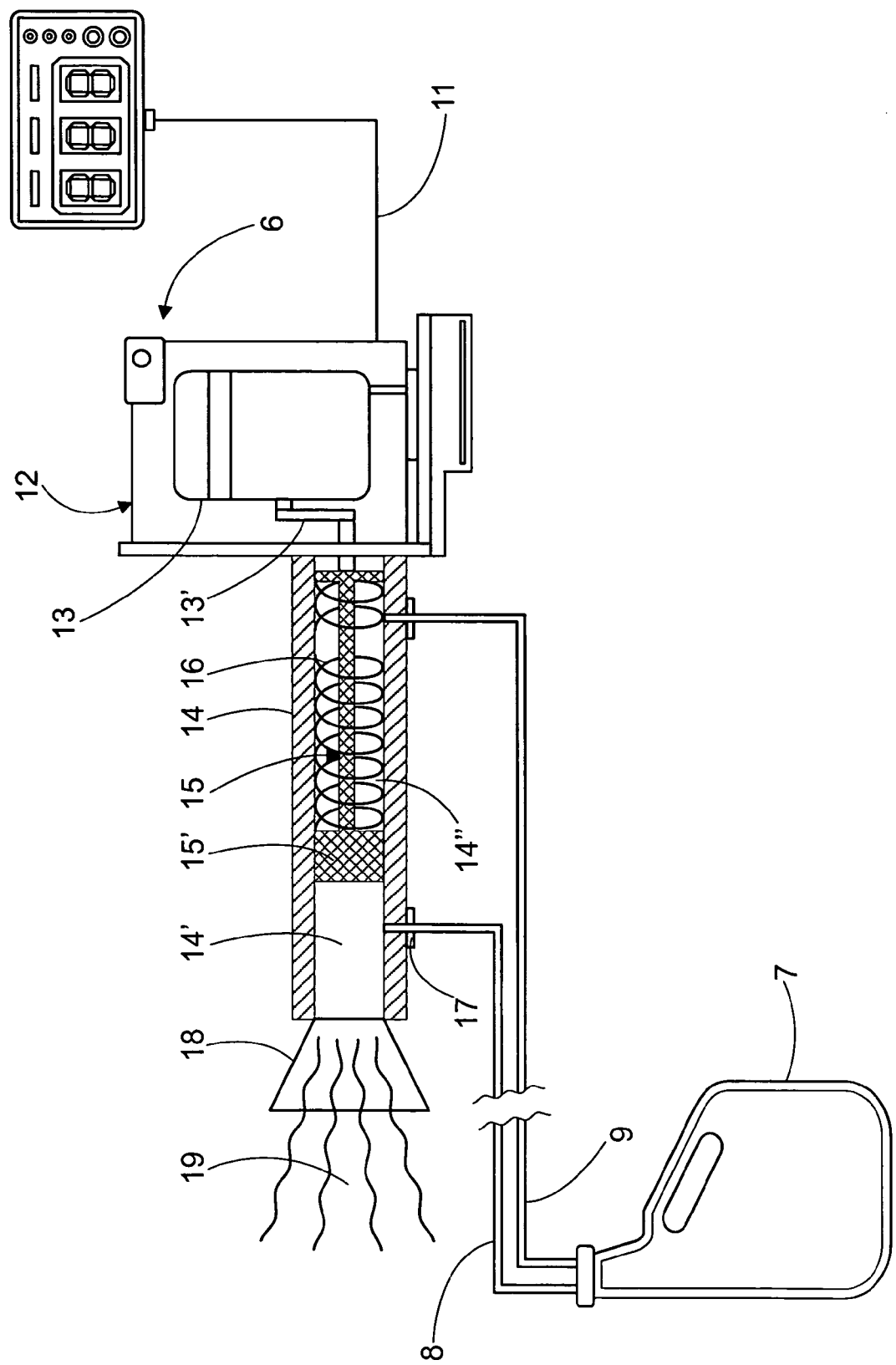
FIG. 2 is a simplified diagram of the parts integrating the device of the invention.

Reference is now made to FIG. 2 of the drawings schematically showing a the sprayer 6, which comprises a driving motor 12, which presents a liquid spraying average rate of 0.2 liters per minute. This sprayer 6 includes an electromagnet 13 and a plate 13' for driving a valve 14, wherein an output chamber 14' and an excess liquid return chamber 14" (liquid flows towards container 7) are defined. A piston 15 that is functionally linked with a spring 16 is placed inside said valve 14. As a result of the movement back of the piston 15, the liquid contained inside jerrycan 7 is aspirated and introduced through opening 17 into valve 14. Eventually, and according to other possible embodiments carried out by any person known in the art, said excess liquid return chamber 14" and consequently said return valve may not be included. This might occur in practice, for instance, in cases where the liquid's returning being not necessary as a result of a very accurate liquid spraying system.

The piston 15 is a solid cylinder made of stainless steel, which is connected through its rear with plate 13' of motor 12. The pushing spring 16, allows the piston 15 to return to the resting position once plate 13' is released. This disposition causes the piston 15 to displace continuously across the valve 14. The piston 15 may be made of bronze or suitable material for that function. Additionally, valve 14 is made of bronze; nevertheless it can be made of another material according to the mechanical requirements of the application.

The conduit 9 is connected to the return chamber 14" of the valve 14, so that in case of the pressure in chamber 14' being too high for reaching a correct spraying operation, the excess liquid can flow through small holes 15'. Thus, when the piston 15 reciprocates, the excess liquid is lead back to the container 7.

The air sprayed by means of a nozzle 18 is aimed towards a sprayed air outlet. This is aligned with the air outlet of said forced ventilation device 1. The liquid is expelled from valve 15 when piston moves forward and when passing through nozzle 18 this liquid, immediately or after passing through conduits 4 and 5 (FIG. 1), contacts the environment and produces a mist 19. This mist 19 is easily spread out as a result of the forced air ventilation system of the device 1.

As shown in FIGS. 1 and 2, nozzle 18, valve 14 and motor 12 can be altogether installed into device 1, or if necessary, they can be installed separately. If, as a result of the features (shape, size, etc.) of the device 1, installing the motor 12 and the valve 14 internally is not possible; they can be installed externally. Even though nozzle 18 has to be installed inside the device 1, this is not a problem, since nozzle 18 is very small and can be connected with valve 14 (installed outside device 1) by means of extensions such as plastic hoses, metallic tubes, etc., achieving this way the same spraying effect. As it can be seen, both jerrycan 7 and the programming panel 10 are placed outside the device 1.

Figure 3:
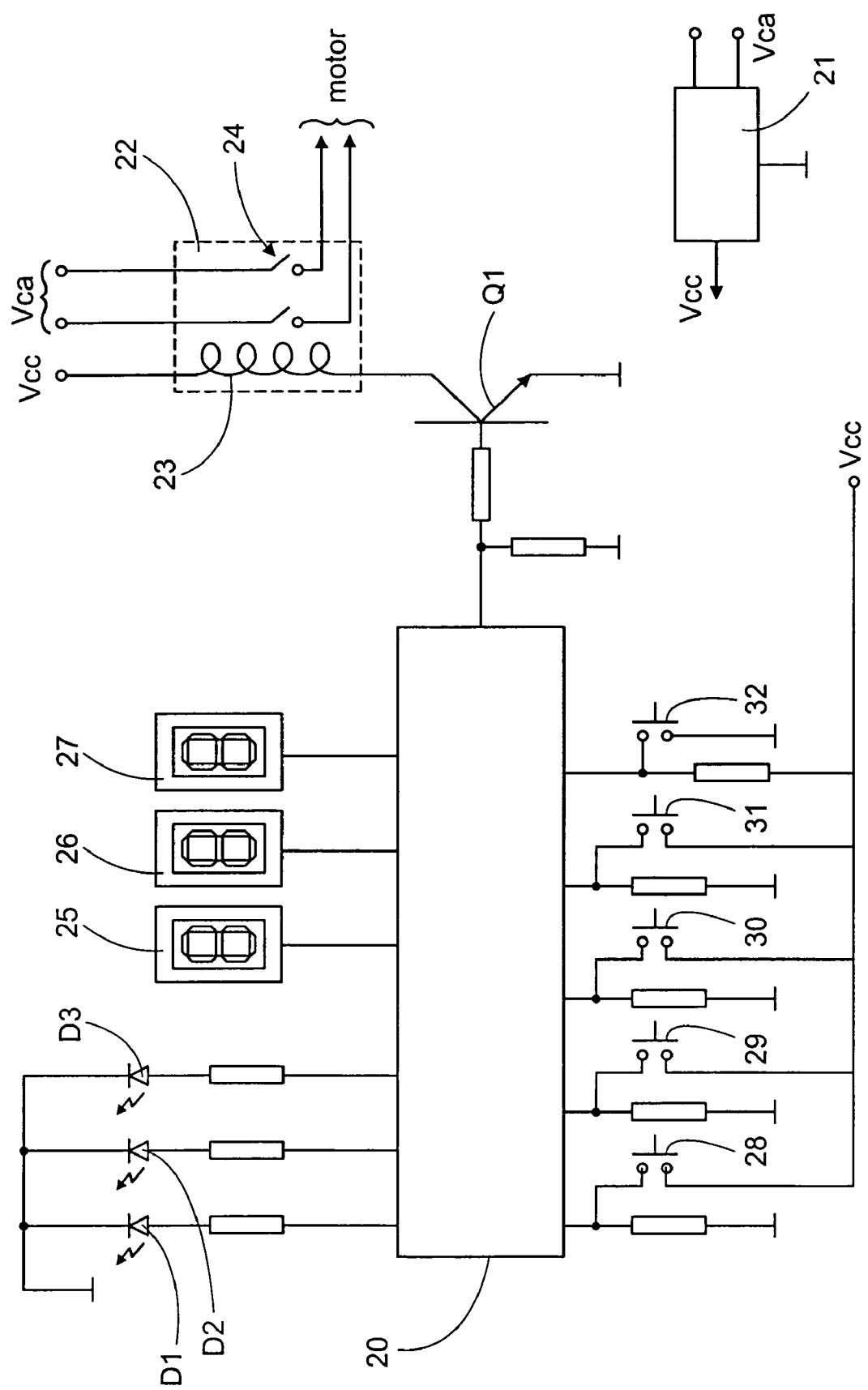
FIG. 3 is a diagram of a first embodiment of a control and programming electronic circuit of the device of the invention.

FIG. 3 shows a circuit for controlling and programming the sprayer 6. This circuit comprises a programmable electronic controller 20 that in the preferred embodiment includes a programmable interrupt controller PIC16C84. This controller 20 is connected through a low voltage power supply 21 to the electric power. Additionally, the controller 20 controls forced ventilation systems of any device that is connected to its terminals or connected to the power key. The controller 20 includes three timing circuits (timers) that switch a transistor Q1, which energizes a coil 23 of a relay 22, thus actuating said relay 22. This way, contacts 24 of said relay 22 can be opened and closed alternatively, thus actuating motor 12 during a period of time previously programmed on the programming panel 10. This programming panel 10 includes a visual indicator or 3 digit display, indicated 25, 26 and 27. This display allows the operator to visualize the operating periods of time programmed for the device.

Said timers operate as described below:

A first timer allows to set up the duration of the first pulse or connection of motor 12 by means of the relay 22, in order to start spraying liquid. This first pulse is programmed for being triggered just two minutes after the forced air ventilation device has been switched on.

A second timer allows the sequencing of a duration after the very moment the air ventilation system was switched on, when the relay 22 has to be actuated again. So, this timer defines the frequency of the sequential activations of said motor 12.

A third timer allows to program how long (in seconds) will be each activation cycle of the motor 12. Thus, the third timer defines the duration of each sequential activation of the motor 12.

Although the triggering time of the first timer can be modified voluntarily by programming the controller 20, in conditioned air devices this time is preferably set to two minutes, because it is considered this is the average time necessary to reach the full operation of these devices (since they have been powered on), when pressure and speed of the airflow generated into the conduits reach their maximum predicted levels. This time will be adjusted in each case in particular according to the most convenient value.

Frequency and activation time of motor 12 are according to the size of the place that is intended to aromatize. This is because the larger the room is, the more quantity of product has to be sprayed.

The first timer (the two-minutes-set timer) starts when the circuit is supplied energy through the power supply 21. During this time, it is possible to access the programming menu by pressing simultaneously a labeled "ENTER" button 28 and a labeled "ESCAPE" button 29. Then, it is possible to set the second timer by means of buttons 30 and 31, which respectively increase or decrease the time. The time set is displayed on displays 25, 26 and 27. Afterward, pressing simultaneously buttons 28 and 29 the third timer may be set. Finally, pressing button 28, or "ENTER", within 3 seconds, saves entered data.

After the programming process has been finished, timer one restarts the two-minutes countdown. After these two minutes expire, this first timer, which has been previously set, is triggered. The relay 22 keeps closed for a T2 time (set in seconds), thus feeding motor 12.

When T2 time has expired, the third timer (T3), which has been set in seconds, is triggered (and displayed in displays 25, 26 and 27). During this time, motor 12 remains off. The second timer (programmed in seconds) triggers when T3 time has expired. Motor 12 remains active during time T2.

Then, the cycle is indefinitely repeated: T3 is triggered, then T2 is triggered, then is triggered T3 again, and so on. These timers respond to their corresponding active cycles previously set.

Light emission devices (LED) D1, D2 and D3, are arranged in order to allow the user to visualize the moment and time of activation of each timer, both when programming the device and when it is operative. These LEDs indicate the triggering of the first timer, the second one and the third one respectively. These LEDs flash once a second indicating which timer is working in that moment.

Since the spraying mechanisms of the present device are activated when the relay 22, which connects the power supply to the motor 12, is energized, so the device may also work according to various configurations. Such configurations or embodiments may include, for example, movement sensors that turn on the controller when detecting something moving in the room, or turn it off when detecting no movement; odor sensors that turn on the relay 22 when detecting that the sprayed liquid in-room concentration is less than a previously set minimum level, or that turn off the system when detecting that this sprayed liquid in-room concentration is greater than a previously set maximum level, or that turn on the device again as a result of detecting some unpleasant smell, for instance the smell resulted of something burning, broken pipes, high temperature, etc. Additionally, a system that can turn on, turn off, or increase the power of the device of the invention according to any schedule, according to the people in the room, etc. can be implemented. This can be done, for instance, by means of schedule timers.

Figure 4:
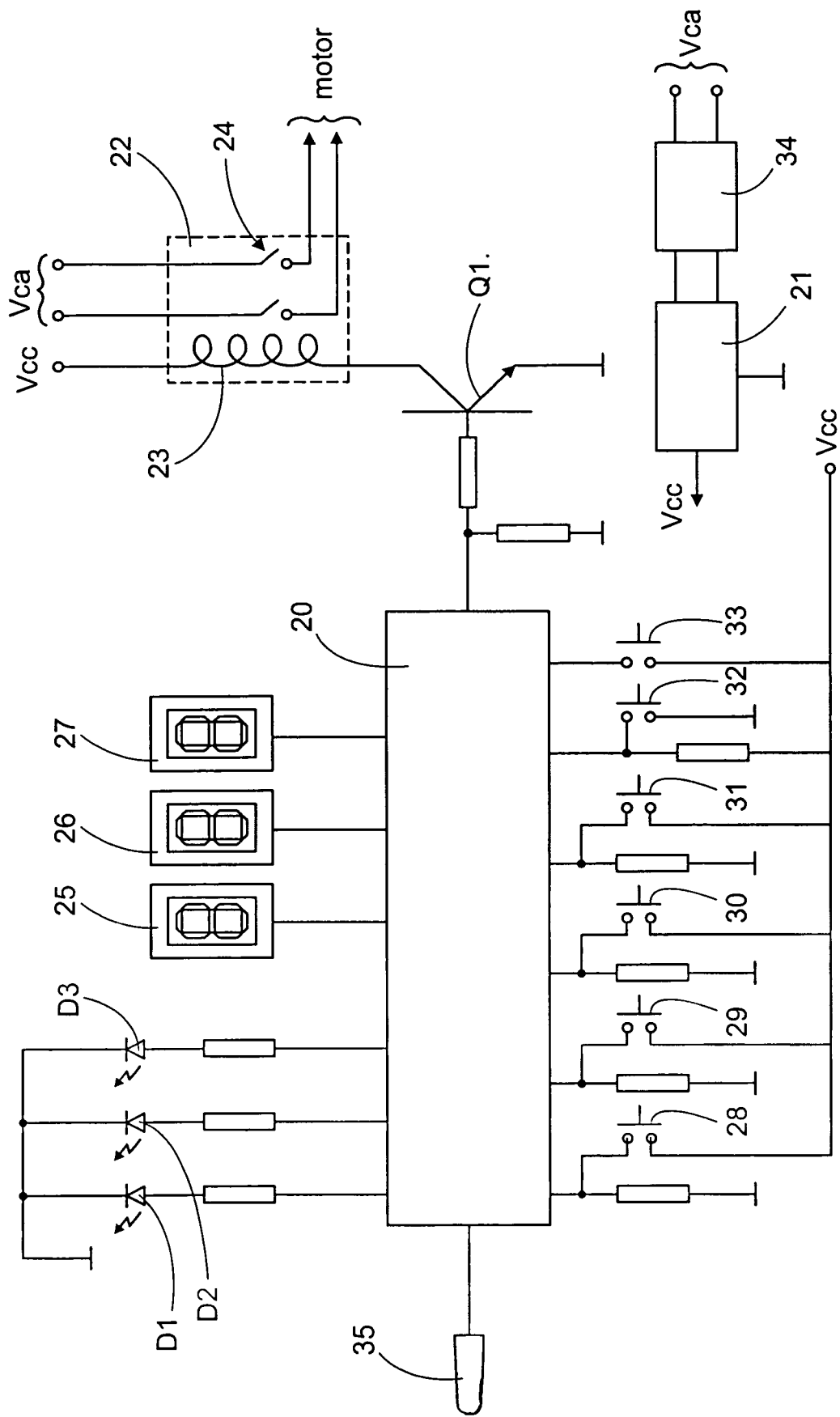
FIG. 4 is a diagram of a second embodiment of the electronic circuit of device of the invention.

The spraying device of the present invention may be preferably connected to the electric connectors of the device 1, in order to turn it on and off according to the operating state of the device 1. In case of this connection not being possible, the device of the present invention can be connected directly to the electrical power line of the facility wherein it is installed, adding a main on-off schedule timer. FIG. 4 shows an exemplary connection that includes a schedule timer 34. This timer can be a conventional one as those used for commanding shop-windows lights, which is connected to the input of the power supply 21. This embodiment allows the schedule timer to determinate, according to its set up data, the start time and the end time of the operative sequences of the three timers that are included in the controller 20.

Furthermore, the embodiment of FIG. 4 shows a sensor (detector) 35, which is connected to the controller 20. This sensor generically represents an environmental conditions sensor, for instance, a temperature sensor, a movement detector, a smell detector, etc., or the combination of several sensors. When sensor 20 is activated as a result of some environmental condition, this sends an electrical signal to controller 20, which energizes relay 22. Consequently, relay 22 activates sprayer motor 12 during the period of time the sensor is sending said electrical signal.

The controller 20 set up is easy, however, qualified and authorized personnel are required. In order to provide the system with security properties, a security procedure has been designed. This procedure makes it possible to prevent set up by unauthorized personnel. The security procedure is defined as a result that programming the device can only be accomplished during the first two minutes the first timer is on, it being impossible to implement any change after this time period. In order to set up the device this has to be turned off and then turned on, in a word, it has to be reset. Moreover, buttons 28 and 29 have to be simultaneously pushed for 3 seconds for programming the device.

A push button 32 is included in the device of the invention in order to reset the timers. This button 32 allows the user to modify the device setup. Additionally a push button 33 defines a control that sends a Vcc signal to the controller 20, which forces the energizing of the relay 22, thus immediately turning on the motor 12. This is useful when changing the container 7 in order to fill with liquid product conduits 8 and 9 and the valve 14. Push button 32 is concealed from behind the box wherein the electronic circuit is placed, so access to it is only possible by means of a special tool. Furthermore, button 33 has no identification label, as the other buttons, in order to prevent its being identified and to prevent any unauthorized person from erroneously programming the device.

Several spraying devices including respective timers 34 can be installed in the same room in order to combine the spraying of several liquid products at different moments, thus achieving a particular effect in each case. This may produce a more pleasant place according to a schedule, and additionally could be used as a commercial aim, for instance producing the environmental smell distinctive of some goods.

As an example, in case of aromatizing a factory, from 8:00 AM to 12:00 PM a product is emittable whose smell stimulates human activity, then, from 12:01 PM to 02:00 PM a smell is emitted that relaxes the personnel at their lunch time, for instance a sweet fragrance could be used, and finally, from 02:01 PM to 06:00 PM other smells may be emitted that again stimulate human activity. In order to do that, three identical spraying devices, each one including its single schedule timer and connected to its own container, have to be used. Additionally, only one container can be employed that includes three different compartments, each one containing a different liquid product.

The device of the invention is intended to be not only an aromatizing device; this may be used, for instance, as a disinfecting device. As a result of its spraying properties, the device could be used for spraying fragrances, germicides, bactericides, insecticides or the like. As an example, it could be used for spraying a bactericide liquid on the filter of a central air conditioner, thus disinfecting the airflow passing thorough this filter. This could be very helpful for hospitals, medical clinics, operating theaters or the similar, wherein air has to be decontaminated, dust free, bacteria free, smoke free, etc. Logically, the implementation of the device of the invention may vary according to the facility wherein this is installed and type of liquid to be sprayed.

Additionally, as it has been mentioned above, the spraying device may be used for commercial aims, for instance, for spraying some smell representative of goods, in order to stimulate people in the room to consume or purchase those goods. Furthermore, it may be used in cinemas or theaters for creating an environment for giving the audience an additional sensation by means of smell. For example, if a beach movie is being screened, a beach fragrance liquid may be sprayed.

In the described preferred embodiment all control buttons are tactile sensitive.

If motor 12 is properly operated, maintenance or cleaning is not required. The only thing to maintain is that the container always has to have liquid product in it. However, this could be corrected by adding a liquid level sensor in the container, being capable of sending an electrical signal to the controller reporting that the container is empty, thus turning off the motor 12 in order to protect it.

Even though examples and preferred embodiments have been used to better understand the invention and its features, these examples are not limitative or restrictive of the scope of protection. On the contrary, it must be clearly understood that many other embodiments, modifications and alterations equivalent to the elements of the invention may be suggested by persons skilled in the art after reading the present description, without departing from the spirit of the present invention and/or the scope of the appended claims.

The invention claimed is:

1. A device for conditioning air by controllably delivering at least one liquid product, the device comprising:
   at least one liquid container for containing at least one liquid to be delivered into the air;
   at least one electromechanical liquid sprayer having a liquid input connected to the at least one container and an output for delivering sprayed liquid;
   electrical motor means for actuating the sprayer;
   at least one device operation programming circuit connected to the motor means, the circuit comprising a programmable electronic controller including a first timing circuit (timer) defining a start time and the operation time of the motor means, a second timer defining a frequency for sequential actuations of the motor means, and a third timer defining a length for each one of said sequential actuations of said motor means.

2. The device of claim 1, further including a programmable timer for enabling the operating sequence of said timers.

3. The device of claim 1, wherein said programmable electronic controller includes a power source connected to a forced air circulation device electrical power input.

4. The device of claim 2, wherein said programmable electronic controller includes a power source connected to a forced air circulation device electrical power input.

5. The device of claim 1, wherein said programmable electronic controller is connected to a sprayed room environmental conditions sensor.

6. The device of claim 2, wherein said programmable electronic controller is connected to a sprayed room environmental conditions sensor.

7. The device of claim 3, wherein said programmable electronic controller is connected to a sprayed room environmental conditions sensor.

8. The device of claim 5, wherein said environmental conditions sensor is a temperature sensor.

9. The device of claim 6, wherein said environmental conditions sensor is a temperature sensor.

10. The device of claim 7, wherein said environmental conditions sensor is a temperature sensor.

11. The device of claim 5, wherein said environmental conditions sensor is a movement detector.

12. The device of claim 6, wherein said environmental conditions sensor is a movement detector.

13. The device of claim 7, wherein said environmental conditions sensor is a movement detector.

14. The device of claim 5, wherein said environmental conditions sensor is an air elements sensor detecting elements in the air that produce unpleasant smells.

15. The device of claim 6, wherein said environmental conditions sensor is an air elements sensor detecting elements in the air that produce unpleasant smells.

16. The device of claim 7, wherein said environmental conditions sensor is an air elements sensor detecting elements in the air that produce unpleasant smells.

17. The device of claim 1, wherein the mechanical system of said electromechanical sprayer is placed into a forced air circulation device, being the pulverized liquid output aligned to the output of the air flow generated by said forced air circulation device, and being the liquid container and a board wherein said device-operation programming circuit is mounted placed outside the forced air circulation device.

18. The device of claim 17, wherein said forced air circulation device is an air conditioner.

19. The device of claim 17, wherein said forced air circulation device is a part of a central air conditioner system.

20. The device of claim 1, wherein said liquid is selected from the group consisting of fragrances, germicides, bactericides, insecticides.

* * * * *